(12) United States Patent
Arad et al.

(10) Patent No.: US 6,888,033 B1
(45) Date of Patent: May 3, 2005

(54) ANTI-VIRAL COMPOUNDS (75) Inventors: Dorit Arad, Tel Aviv (IL); Yuval Elias, Tel Aviv (IL); Orna Elhanany, Tel Aviv (IL); Michael Shokhen, Kvar Sava (IL); Leopold Puzis, Bene Aish (IL)

(73) Assignee: Cytoclonal Pharmaceutics, Inc., Dallas, TX (US)

( * ) Notice: Subject to any disclaimer, the term of this patent is extended or adjusted under 35 U.S.C. 154(b) by 0 days.

(21) Appl. No.: 09/202,359

(22) PCT Filed: Jun. 15, 1997

(86) PCT No.: PCT/IL97/00193

§ 371 (c)(1),
(2), (4) Date: May 21, 1999

(87) PCT Pub. No.: WO97/47270

PCT Pub. Date: Dec. 18, 1997

(30) Foreign Application Priority Data

Jun. 14, 1996 (IL) .................................................. 118657

(51) Int. Cl.$^7$ ............................................. C07C 49/76
(52) U.S. Cl. ........................................ 568/335; 568/308
(58) Field of Search ................................. 568/308, 335

(56) References Cited

U.S. PATENT DOCUMENTS

| | | | | |
|---|---|---|---|---|
| 3,657,436 A | * | 4/1972 | Berger ........................ | 424/244 |
| 3,666,771 A | * | 5/1972 | Hoefle et al. ............ | 548/265.6 |
| 3,956,375 A | * | 5/1976 | Farkas et al. ................. | 560/53 |
| 4,327,088 A | * | 4/1982 | Shinma et al. .............. | 514/125 |
| 4,333,941 A | * | 6/1982 | Baratz ........................ | 424/267 |
| 4,503,256 A | * | 3/1985 | Fourie et al. ............... | 549/405 |
| 4,578,520 A | * | 3/1986 | Fourie et al. ............... | 568/315 |
| 4,605,674 A | * | 8/1986 | Fujiu et al. .................. | 514/277 |
| 4,816,487 A | * | 3/1989 | Schewe et al. ............. | 514/640 |
| 5,091,171 A | * | 2/1992 | Yu et al. ...................... | 424/642 |
| 5,100,893 A | * | 3/1992 | Stokbroekx et al. ... | 514/217.05 |
| 5,276,058 A | | 1/1994 | Satoh et al. ................. | 514/646 |
| 5,324,743 A | | 6/1994 | Dillard et al. .............. | 514/456 |
| 5,356,620 A | * | 10/1994 | Yamamoto ............... | 424/78.04 |
| 5,359,098 A | * | 10/1994 | Erickson et al. ........... | 549/400 |
| 5,514,778 A | | 5/1996 | Hammond et al. ......... | 530/333 |
| 5,545,653 A | * | 8/1996 | Miller ........................ | 514/388 |
| 5,643,929 A | * | 7/1997 | Diana ......................... | 514/364 |
| 6,017,957 A | * | 1/2000 | Skolnick et al. ............ | 514/531 |
| 6,020,371 A | * | 2/2000 | Dragovich .................. | 514/514 |
| 6,087,374 A | * | 7/2000 | Schladetzky ................ | 514/303 |
| 6,248,306 B1 | * | 6/2001 | Schmitt-Willich et al. . | 424/1.65 |
| 6,369,057 B1 | * | 4/2002 | Billhardt et al. ......... | 514/234.8 |

FOREIGN PATENT DOCUMENTS

| | | |
|---|---|---|
| EP | 0004579 | 10/1979 |
| NZ | 0154883 | 6/1972 |
| NZ | 0161750 | 9/1972 |
| NZ | 0167900 | 1/1974 |
| NZ | 0189141 | 8/1980 |
| NZ | 0183860 | 7/1984 |

OTHER PUBLICATIONS

Singh, Tetrahedron Letters 32, 5279, 1991.*
Allaire, Nature 369, pp. 72–76, May 1994.*
Carthy, Clin. Exp. Pharm. Physiol. 24, 997–1003, Dec. 1997.*
Ando, R. & Isaka, Y., 1993. "A new class of proteinase inhibitor. Cyclopropenone–containing inhibitor of papain," *J. Am. Chem. Soc.* 115:1174–1175.
Arad, D., et al., 1990. "A simulation of the sulfur attack in the catalytic pathway for papain using molecular mechanics and semiempirical; quantum mechanics," *J. Am Chem Soc.* 112:491–502.
Arad, D. et al., 1993. "Structural and mechanistic aspects of 3C proteases from the picornavirus family," *J. Chem. Inf. Comput. Sci.* 33:345–349.
Asboth, B. and Polgar, L., 1983. "Transition–state stabilization at the oxyanion binding sites of serine and thiol proteinases: hydrolyses of thiono and oxygen esters," *Biochemistry.* 22:117–122.
Bromme, D., et al., 1996. "Peptidyl vinyl sulphones: a new class of potent and selective cysteine protease inhibitors," *Biochem. J.* 315:85–89.
Cordingley, et al. 1990. "Substrate requirements of human rhinovirus 3C protease for peptide cleavage in vitro," *J Biol Chem* 265:9062–9065.
De Meyer, N., et al., 1991. "4'–Hydroxy–3–methoxyflavones with potent antipicornavirus activity," *J. Med. Chem.* 34(2):736–746.
Greenaway, W., et al., 1992 "Analysis of phenolics of bud exudates of *Populus koreana, Populus maximowiczii,* and *Populus suaveolens* by GC–MS," *Z. Naturforsch.* 47c:313–317.
Kreisberg, R. et., 1995 "Mechanistic and structural features of the picornaviral 3C protease," *Organic reactivity: Physical and Biological Aspects.* pp. 110–122.

(Continued)

Primary Examiner—Christopher S. F. Low
Assistant Examiner—David Lukton
(74) Attorney, Agent, or Firm—Sidley Austin Brown & Wood LLP (57) ABSTRACT

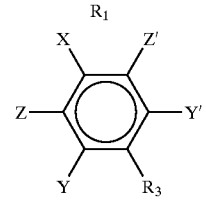

A compound having the formula (I) wherein the substituents are defined herein. Also provided are pharmaceutical compositions including a compound of formula (I) in a pharmaceutical carrier, for treating a disease caused by a picornavirus. Also provided is a method of treating a subject with a disease caused by a picornavirus, including a compound of formula (I) in a pharmaceutical carrier.

1 Claim, 5 Drawing Sheets

OTHER PUBLICATIONS

Lau, C.K., et al., 1989. "Synthesis and structure –activity relationships of a novel class of 5–lipoxygenase inhibitors. 2–(Phenylmethyl)–4–hydroxy–3,5–dialkylbenzofurans: The development of L–656,224," *J. Med. Chem.* 32(6):1190–1197.

Lin, Y. and Welsh, W.J., 1996. "Molecular modeling of substrate –enzyme reactions for the cysteine protease papain," *J. Molecular Graphics.* 14:62–72.

Looker, J.H., et al., 1984. "5,8–Quinoflavone. Synthesis and addition reactions," *J. Org. Chem.* 49(4):645–649.

Masento, M.S., et al., 1988. "Differentiation–inducing factor from the slime mould *Dictyostelium discoideum* and its analogs," *Biochem. J.* 256:23–28.

Matthews, et al., 1994. "Structure of human rhinovirus 3 protease reveals a trypsin–like polypeptide fold, RNA–b-inding site, and means for cleaving precursor polyprotein," *Cell.* 77(5):761–771.

Menard, R. et al., 1991. "Contribution of the glutamine 19 side–chain to transition–state stabilization in the oxyanion hole of papain," *Biochemistry.* 30:8924–8928.

Morandini, P., et al., 1995. "The proximal pathway of metabolism of the chlorinated signal molecule differentiation–inducing factor—1 (DIF–1) in the cellular slime mould *Dictyostelium*," *Biochemical Journal.* 306:735–743.

Polgar, L. and Asboth, B., 1986. "The basic difference in catalyses by serine and cysteine proteinases resides in charge stabilization in the transition state," *J. Theor. Biol.* 121:323–326.

Rasnick, D. 1996. "Small synthetic inhibitors of cysteine proteases," *Perspectives in Drug Discovery and Design.* 6:47–63.

Schroder, E., et al., 1993. "X–ray crystallographic structure of a papain–leupeptin complex," *FEBS Lett.* 315:38–42.

Shokhen, M. and Arad, D., 1996. "The source for the difference between sulfhydryl and hydroxyl anions in their nucleophilic addition reaction to a carbonyl group: A DFT approach," *J. Moleculare Model.* 2:399–409.

Storer, A. C. and Menard, R., 1994. "Catalytic mechanism in papain family of cysteine peptidases," *Methods enzymol.* 244:486–500.

Vernet, T., et al., 1995. "Structural and functional roles of asparagine 175 in the cysteine protease papain," *J. Biol Chem.* 270:16645–16652.

*The Merck Index.* 1989. "Salicylaldehyde," S. Budavari, Ed., 11th Edition, Merck & Co., Inc., Rahway, N.J., p. 1323, No. 8295.

*The Merck Index.* 1989. "Ethyl Salicylate," S. Budavari, Ed., 11th Edition, Merck & Co. Inc., Rahway, N.J., p. 605, No. 3804.

*The Merck Index.* 1989. "Benzyl Salicylate," S. Budavari, Ed., 11th Edition, Merck & Co., Inc., Rahway, N.J., p. 179, No. 1160.

Kenny et al., 1985. "In Vitro and In Vivo Antipicornavirus Activity of Some Phenoxypyridinecarbonotrile", *Antimicrobial Agents and Chemotherapy.* vol. 28, No. 6, pp. 745–750.

Morris et al. 1987. "Chemical Struture Of The Morphogen Differentiation Inducing Factor From Dictyostelium Discoideum," *Nature.* vol. 328, No. 6133, pp. 811–814.

*The Merck Index.* 1989. "Salicylic Acid," S. Budavari, Ed., 11th Edition, Merck & Co., Inc., Rahway, N.J., p. 1324, No. 8301.

* cited by examiner

Figure 1

|  | p10 | p9 | p8 | p7 | p6 | p5 | p4 | p3 | p2 | p1 | p1' | p2' | p3' | p4' | p5' | p6' | p7' | p8' | p9' | p10' |
|---|---|---|---|---|---|---|---|---|---|---|---|---|---|---|---|---|---|---|---|---|
| POL1M | i | g | n | c | m | e | a | l | F | Q | G | p | l | q | y | k | d | l | k | i |
| POL1S | i | g | n | c | m | e | a | l | F | Q | G | p | l | q | y | k | d | l | k | i |
| POL32 | i | g | n | c | m | e | a | l | F | Q | G | p | l | q | y | k | d | l | k | i |
| POL3L | i | g | n | c | m | e | a | l | F | Q | G | p | l | q | y | k | d | l | k | i |
| COXA2 | i | g | n | c | m | e | a | l | F | Q | G | p | l | r | y | k | d | l | k | i |
| COXA4 | i | g | n | c | m | e | a | l | F | Q | G | p | i | q | y | r | d | v | m | i |
| BOVEV | i | g | n | v | l | e | a | l | F | Q | G | p | v | c | y | k | p | l | r | i |
| COXA9 | v | g | a | t | l | e | a | l | F | Q | G | p | p | i | y | r | e | i | k | i |
| COXB1 | v | g | a | t | l | e | a | l | F | Q | G | p | p | i | y | r | e | i | k | i |
| COXB5 | v | g | a | t | l | e | a | l | F | Q | G | p | p | i | y | r | e | i | k | i |
| EC11G | v | g | a | t | l | e | a | l | F | Q | G | p | p | i | y | r | e | i | k | i |
| COXB4 | v | g | a | t | l | e | a | l | F | Q | G | p | p | v | y | r | e | i | k | i |
| SVDVH | v | g | a | t | l | e | a | l | F | Q | G | p | p | v | y | r | e | i | k | i |
| SVDVU | v | g | a | t | l | e | a | l | F | Q | G | p | p | v | y | r | e | i | k | i |
| COXB3 | v | g | t | t | l | e | a | l | F | Q | G | p | p | v | y | r | e | i | k | i |
| HUEV7 | t | q | d | k | l | e | a | l | F | Q | G | p | p | t | f | k | e | i | k | i |
| HRV1B | v | v | d | v | m | s | a | i | F | Q | G | p | i | s | l | d | a | p | p | p |
| HRV2 | v | v | d | v | m | t | a | i | F | Q | G | p | i | d | m | k | n | p | p | p |
| HRV89 | a | a | q | a | m | e | a | i | F | Q | G | i | d | l | q | s | p | p | p | p |
| HRV14 | i | t | d | s | l | e | t | l | F | Q | G | p | v | y | k | d | l | e | i | d |

R''' = aromatic ring

Figure 2A (con't)

3.

R''' = Small or branches aliphatic like side chain of Leu, Val, Ile o

Figure 2A (con't)

4.

$R_1 =$

Etc.

$R_1 =$

Etc.

$R_1 =$  Or

Etc.                Etc.

Figure 2B

ANTI-VIRAL COMPOUNDS

FIELD AND BACKGROUND

The present invention concerns compounds with anti-viral activity, including novel inhibitors of the 3C, 2A and 3C-like cysteine proteases or picornaviridae and related viruses (see Gorbalenya, Prospective Drug Discovery Design, 6: 64–86, 1996).

The picornavirus family encompasses single-stranded positive-sense RNA viruses, encapsulated in a protein capsid (Reviewed in Rucekert, 1996, i Fields, *Virology*, 609–654). These viruses cause a wide range of diseases in humans and other mammals, including the common cold (rhinoviruses), gastro-intestinal ailments (enteroviruses, such as coxsack-ievirus and echovirus), poliomyelitis (the enterovirus poliovirus), heart diseases (cardioviruses), hepatitis (hepatitis A) and foot and mouth disease (aphtoviruses). Rhinoviral common cold is of specifically noted medical and economical significance, due both to is ubiquity (the major cause of acute illness in the United States) and to the debilitating effect of the disease and consequential loss of work days (see McKinlay, *Ann. Rev. Microbiol.*, 46:635–54, 1992). Related viral families of the picornavirus supergroup, such as flaviviridae and potyviridae, cause various diseases in agriculturally significant crops, such as potatoes (see Ryan, J. Gen. Virol., 4:699–723, 1997).

After infection of the host cell, the picornaviral RNA is translated into a single polyprotein which has auto-catalytic proteolytic activity, cleaving itself into mature viral proteins. The 2A and 3C proteolytic enzymes, which are part of the picornaviral autocatalytic polyproteins, are responsible for these cleavages. The 2A protease cleaves co-translationally between the structural and non-structural protein precursors and the 3C protease cleaves most of the remaining sites post-translationally.

The 3C and in some cases 2A, proteases are responsible for maturation of the picornavirus and are crucial for completion of the picornaviral life cycle. As a result, the 3C protease has been a prime target for existence structural and mechanistic investigations during the last few years, and its mechanism of action and structural features has been determined (Kreisberg et al, *Organic Reactivity: Physical and Biological Aspects*, 110–122 (1995)).

The 3C and 2A proteases have somewhat different specificities for substrates. Furthermore, the two proteases have different mechanisms of action because the 2A protease requires zinc, while the 3C protease does not.

Attempts to find treatments for diseases caused by a picornavirus species have been largely directed towards finding inhibitors for the 3C protease, since such inhibition would prevent production of new virions as there are no native cellular proteases which can replace the cleavage activity of these viral proteases. Therefore, finding an efficient inhibitor of 3C picornavirus protease activity, or of other viral activity, would be valuable for the treatment of a large number of viral diseases, both in humans and in lower animals.

The first inhibitor of the 3C protease to be found by screening was thysanone, an antibiotic compound obtained from *Thysanphora penicilidies* (Singh et al, *Tetrahedron Lett.*, 32: 5279–82 (1991)). However, this compound was not developed into a pharmaceutical composition, since it exhibited modest protease inhibitory activity and was found to be an inhibitor of the elastase enzyme present in erythrocytes.

Two additional antibiotic compounds, of fungal origin, termed citrinin hydrate and radicinin were obtained by screening over 20,000 microbial extracts (Kadam et al. *J. Antibiotics* 7: 836–839 (1994)). These two compounds were weaker inhibitors of picornaviral proteases than thysanon. In this same screening process, a new compound termed kalafungin, which is also an antibiotic compound, was discovered by structural comparison to radicinin. Kalafungin was found to be a better inhibitor, by three orders of magnitude, than radicionin an citrinin hydrate (McCall et al, *Biotechnology*, 12: 1012–1016 (1994)). However, none of these inhibitors has yielded a clinically useful compound, combining high anti-viral activity but low toxicity.

Another group of inhibitors, substituted isatins, has also been examined (S. E. Webber et al., *Med. Chem.*, 39:5072–5082, 1996). Certain members of this group show significant inhibition of 3C proteases with concentrations in the nmolar range, but are highly toxic. Other members of the group are relatively non-toxic, but have poor anti-viral activity. Thus, none of the background art compounds combine strong protease inhibitor or anti-viral effects with low toxicity.

There is therefore an unmet medical need for new compounds which have strong anti-viral activity against the picornaviruses.

SUMMARY OF THE INVENTION

It is an object of the present invention to provide novel derivatives of the known differentiation factor DIF1 which have anti-viral and protease inhibitory activity. It is another object of the present invention to provide pharmaceutical compositions which use these derivatives, as well as DIF1, to treat a disease caused by a picornavirus. It is yet another object of the present invention to provide methods of use of these pharmaceutical compositions to treat a disease caused by a picornavirus. It is still another object of the present invention to provide a method for the detection of a picornavirus.

According to the present invention, there is provided a compound of the formula (I):

wherein:

X is selected from the group consisting of C=O, S=O, C=S, (C=O)—N, (C=O)—O and (C=O)—S.

$R_1$ is selected from the group consisting of:
(i) hydrogen, hydroxyl or a hydrocarbon chain of from about 1 to about 10 carbons long selected from the group consisting of saturated, unsaturated and fluorinated, wherein said hydrocarbon chain is unsubstituted or substituted with at least one $R^{11}$, wherein $R^{11}$ is selected from the group consisting of:
(ia) $C_1$–$C_4$ alkyl, $C_2$–$C_4$ alkenyl, $C_3$–$C_8$ cycloalkyl, $C_6$–$C_{10}$ bicycloalkyl, benzo-fused or aryl which may be substituted or unsubstituted;
(ib) halogen, cyano, nitro, amino, hydroxy, adamantyl, carbamyl, carbamyloxy or keto;
(ic) an oligopeptide of 1–3 amino acid residues; and
(id) $NR^{13}R^{14}$, $CO_2R^{13}$, $O(C=OR^{13})$, $SO_2R^{14}$, $SOR^{14}$, $(C=O)NR^{13}R^{14}$, or $NR^{14}(C=O)R^{13}$;
wherein:
$R^{13}$ is selected from the group consisting of hydrogen, phenyl, benzyl, $C_1$–$C_6$ alkyl and $C_3$–$C_6$ alkoxyalkyl; and R$^{14}$ is selected from the group consisting of hydrogen, hydroxy, C$_1$–C$_4$ alkyl and benzyl;

(ii) an oligopeptide of 1 to 5 amino acids or a pepidomimetic molecule having substantially similar binding properties as the oligopeptide; and (iii) C$_3$–C$_8$ cycloalkyl and C$_6$–C$_{10}$ bicycloalkyl, C$_3$–C$_7$ cycloalkylmethyl, a benzo-fused phenyl, or a C$_5$–C$_8$ heterocyclic ring system including at lest one nitrogen, oxygen or sulfur atom, which may be additionally substituted with R$^{11}$ as defined above;

R$^3$ is selected from the group consisting of:

(i) hydrogen, phenyl, hydroxyl, C$_1$–C$_{12}$ hydrocarbon chain or O—C$_1$—C$_{12}$ hydrocarbon chain which may be additionally substituted with at least one R$^{11}$ as defined above; and (ii) an oligopeptide of 1 to 3 amino acids, an oligopeptide of 1 to 3 amino acids joined to the backbone by an oxygen, or a peptidomimetic;

Z is selected from the group consisting of hydroxyl, sulfhydryl, amino, carboxyl and NHR$^{11}$, wherein R$^{11}$ is defined as above;

Z' is selected from the group consisting of:

(i) hydroxyl, amino, carbamido, carbamyl, carbamyloxy or halogen;

(ii) hydrogen; and (iii) C$_1$–C$_4$ alkyl, C$_2$–C$_5$ alkenyl, C$_3$–C$_8$ cycloalkenyl, or C$_1$–C$_5$ alkoxy which may be additionally substituted with at least one R$^{11}$ as defined above;

Y and Y' are independently selected from the group consisting of:

(i) hydrogen, halogen, C$_1$–C$_4$ haloalkyl, or C$_1$–C$_4$ haloalkoxy;

(ii) carbamyl, carbamido, cyano, keto, vinyl, sulfoxide, nitro, C$_1$–C$_3$ alkylsulfonyl, sulfonate or sulfone; and (iii) C$_1$–C$_3$ alkyl which may be additionally substituted with at least one R$^{11}$ as defined above; and (iv) an oligopeptide of 1 to 3 amino acids or a peptidomimetic; and alternatively Z' and R$_1$ collectively form a ring system selected from the group consisting of:

(a) C$_5$–C$_8$ carbocyclic ring which may be saturated or unsaturated, and which may be additionally substituted with at least one R$^{11}$ as defined above; and

(b) C$_5$–C$_{10}$ heterocyclic ring system which may be saturated or unsaturated and which includes at least one nitrogen, oxygen or sulfur atom, and which may be additionally substituted with at least one R$^{11}$ as defined above;

and pharmaceutically acceptable salts thereof;

with the proviso that when X—R$_1$ is a fluorinated keto acyl, Z is hydrogen.

According to preferred embodiments of the present invention, R$_1$ and R$_3$ are each independently oligopeptides, peptidomimetic molecules of these oligopeptides, or substituted or unsubstituted, saturated or unsaturated, hydrocarbon chains which may be straight, branched or cyclic.

Examples of specific compounds according to the present invention are compounds of the following formulae II–XVII, it being noted that these compounds are all specific examples of compounds of formula I:

(II-DIF1)

It should be noted that DIF1 is a known molecule, and that furthermore in this rendition, X—R$_1$ is (C=O)—(CH$_2$)$_4$—CH$_3$, Z and Z' are both hydroxyl, Y and Y' are both Cl and R$_3$ is O—CH$_3$. However, although the molecules itself is known, the novel effects and uses of DIF1, as a viral protease inhibitor and as an anti-viral compound, which are disclosed herein were neither suggested nor taught in the prior art. Indeed, in the prior art DIF1 is known only as a differentiation factor.

(III)

(IV)

(V)

(VI)

-continued

(VII)

(VIII)

(IX)

(X)

-continued (XI)

(XII)

(XIII)

It should be noted that $R_4'$, $R_4''$, $R_5'$ and $R_5''$ are all preferably $R^{11}$ as defined herein.

(XIV)

(XV)

(XVI)

(XVII)

In another embodiment of the present invention, there is provided a composition for treating a disease caused by a picornavirus species comprising a pharmaceutically effective amount of a compound of formula I in combination with a pharmaceutically acceptable carrier.

In yet another embodiment of the present embodiment, there is provided a method of manufacturing a medicament for treating a disease caused by a picornavirus species, comprising the step of placing a pharmaceutically effective amount of a compound of formula I in a pharmaceutically acceptable carrier.

According to another embodiment of the present invention, there is provided a method for the treatment of a disease caused by a picornavirus species in a subject, including the step of administering a pharmaceutically effective amount of a compound of formula I to the subject.

In yet another embodiment of the present invention, there is provided a composition for inhibiting a 3C protease or a cysteine protease with an active site similar to the active site of a 3C protease, the composition including a compound of formula (I). Hereinafter, the term "cysteine protease with an active site similar to the active site of a 3C protease" or "3C-like protease" includes cysteine proteases with an active site having a catalytic dyad of Histidine and Cysteine.

According to still another embodiment of the present invention, there is provided a method for determining the presence of a picornavirus species in a sample including the steps of: (a) conjugating the compound of formula 1 to a detectable label to form a labelled compound; (b) contacting the labeled compound with the sample under conditions enabling binding between the inhibitor and viral proteins; and (c) determining whether any proteins in the sample are bound to the inhibitor, a positive answer indicating the presence of a picornavirus species in the sample.

DESCRIPTION OF THE INVENTION

Unexpectedly, it has been found that the compound identified as DIF1 is a specific inhibitor of the picornavirus 3C protease, and does not inhibit other proteases normally present in the cell. Even more unexpectedly, it has been found that various derivatives and isomers of DIF1 have stronger inhibitory activity than the native compound. Furthermore, these derivatives and isomers also display strong anti-viral activity in whole-cell assays and show substantially low toxicity.

Without desiring to be limited to a single mechanism, the compounds of the present invention appear to have at least part of their anti-viral effect by selectively binding to the picornaviral proteases, essentially in a similar manner as the virally coded natural substrate of the proteases. However, since these compounds are not cleaved, they remain at the binding site of the enzyme, preventing it from cleaving the natural substrate. This competition serves to inhibit viral maturation and thus to inhibit disease progression in vivo.

The parent compound of the inhibitors of the present invention, DIF1 (Differentiation Inducing Factor 1), is chemically defined as 1-(3,5-dichloro-2,6-dihydroxy-4-methoxyphenyl)-hexan-1-one (Morris et al, Nature, 328: 811–814 (1987)). Iso-DIF1, a related compound, is chemically defined as 1-(3,5-dichloro-2,4-dihydroxy-6-methoxyphenyl)-hexan-1-one. DIF1 has been isolated from the cells of the slime mold Dictyostelium discoideum. This mold grows in the single-cell form, but when starved the cells aggregate to form a multi-cellular organism which transforms itself into a migrating 'slug'. Within this slug there is a simple spacial pattern of cell differentiation with prestalk cells in the anterior and prespore cells in the posterior. This pattern reflects the final stalk/spore propagation of the mature fruiting body. Stalk-cell differentiation in vitro can be induced by DIF1 (Town et al. Nature, 202: 717–719 (1976); Brookman et al, Dev. Biol., 91: 191–196 (1982)). Recently, it has been found that DIF1 induces differentiation of murine human undifferentiated leukemia into haemoglobin-synthesizing erythrocyte-like cells (Asahi et al, Bioch. Biophy. Res. Com., 208 (3): 1036–1039 (1995)). The prior art recognizes the role of DIF1 as a general differentiation factor in a number of species.

The particularly strong activity of DIF1 as a picornavirus protease inhibitor is very unexpected, however. Furthermore, inhibitors of 3C picornavirus protease have also been shown to be efficient inhibitors of 2A picornavirus protease, so that the inhibitors of the present invention may also be used to inhibit the 2A protease (Yiu S. F. et al, Virology, J. 615–625 (1991)).

As will be no doubt appreciated by the person versed in the art. Formula 1 above includes a large number of possible compounds, some of which are more effective inhibitors of 3C and 2A proteases than others. Furthermore, other additions can be made to the substitute groups of the compounds of Formula I for other types of functionality.

For example, optionally the hydrocarbon of $R_3$ bears a label such as a radioisotope, a fluorescent label, or a member of the pair biotin/avidin and the like. These detectable labels will enable specific determination of the presence of 3C or 2A picornavirus proteases in a sample indicative of a picornaviral infection. $R_3$ may also bear a cytotoxic moiety capable of destroying the cell harboring the picornavirus, or a specific marker which promotes intracellular degradation. In such a case the specific compound of the invention is used to target the cytotoxic moiety, or degradation marker, specifically to the picornavirus.

Preferred compounds of the present invention include the following compounds of the formula (I):

(I)

wherein X is preferably selected from the group consisting of C=O and (C=O)—N.

Preferably, Z is hydroxyl. Also preferably, Z' is selected from the group consisting of:
(i) hydroxyl, amino, carbamido, carbamyl, carbamyloxy or halogen;
(ii) hydrogen; and
(iii) $C_1$–$C_4$ alkyl, or $C_1$–$C_3$ alkoxy which may be additionally substituted with at least one $R^{11}$ as defined above. More preferably, there are 0–2 $R^{11}$ groups as defined above.

Figure 2A:
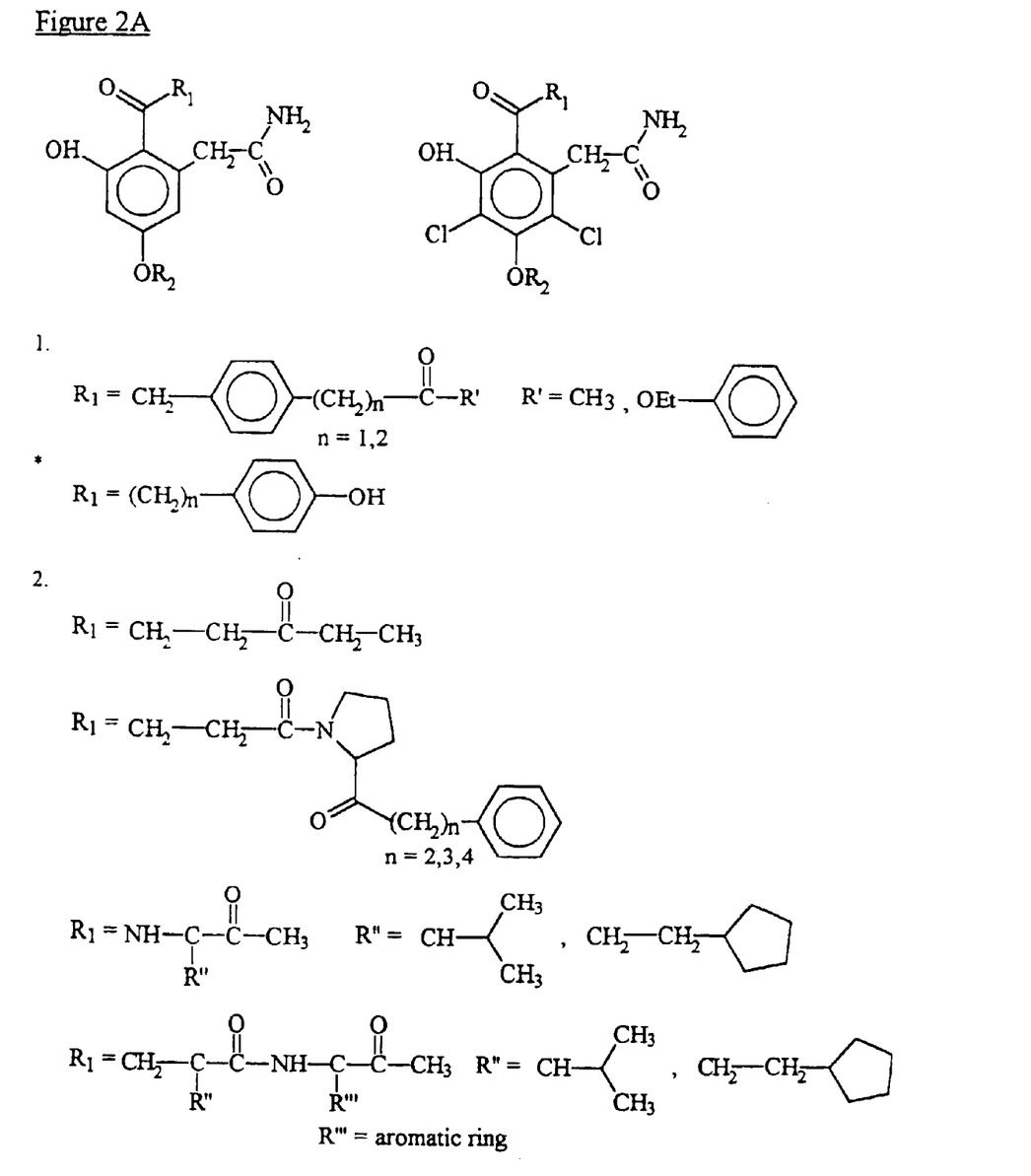
Figure 2B:
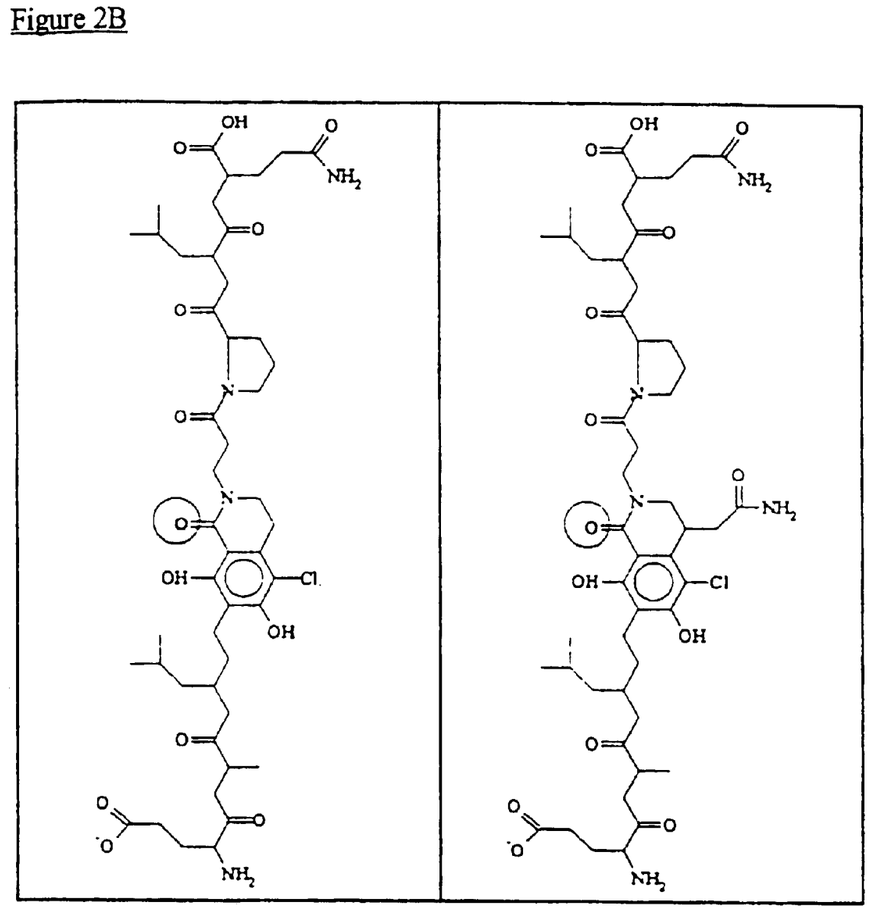

Alternatively, $R_3$ can be an oligopeptide of 3 to 12 amino acid units, preferably an oligopeptide capable of binding to the 3C active site. Various examples of $R_3$ suitable as substitutes in compounds against specific viruses are depicted in FIG. 2 for purposes of illustration only. Optionally, $R_3$ can be a fragment of the amino acid sequences depicted in FIG. 2. $R_3$ can also be a peptidomimetic molecule.

In accordance with one embodiment of the invention $R_1$ is selected from the group consisting of hydrogen, hydroxyl or a hydrocarbon chain of from about 1 to about 10 carbons long selected from the group consisting of saturated, unsaturated and fluorinated, wherein the hydrocarbon chain is unsubstituted or substituted with at least one $R^{11}$, wherein $R^{11}$ is preferably selected from the group consisting of:
(ia) $C_1$–$C_4$ alkyl, or aryl which may be substituted or unsubstituted;
(ib) halogen, cyano, nitro, amino, hydroxy, adamantyl, carbamyl, carbamyloxy or keto;
(ic) an oligopeptide of 1–3 amino acid residues; and
(id) $CO_2R^{13}$, $O(C=OR^{13})$, $(C=O)NR^{13}R^{14}$, or $NR^{14}(C=O)R^{13}$;
wherein:
$R^{13}$ is selected from the group consisting of hydrogen, phenyl, benzyl, $C_1$–$C_6$ alkyl and $C_3$–$C_6$ alkoxyalkyl; and
$R^{14}$ is selected from the group consisting of hydrogen, hydroxyl, $C_1$–$C_4$ alkyl and benzyl.
Preferably, there are from 1 to 3 $R^{11}$ groups.

According to another embodiment of the present invention, $R_1$ is selected from the group consisting of $C_3$–$C_8$ cycloalkyl and bicycloalkyl, $C_3$–$C_7$ cycloalkylmethyl, $C_{7-10}$ arylalkyl, which may be additionally substituted with $R^{11}$ as defined above.

Alternatively, $R_1$ is an oligopeptide of 1 to 5 amino acid units capable of specifically recognizing and binding to the active site of the species-specific 3C protease against which the inhibitor is directed, since the active site of each 3C protease differs slightly from one type of picornavirus to the other. Generally speaking, the oligopeptide should be able to mimic the amino acid sequence of the viral proteins to which the 3C protease binds; some of these amino acids are conserved and common to all picornaviruses, while others vary between the sub-families and species. This description is true for all oligopeptides disclosed as substituents herein.

Figure 1:
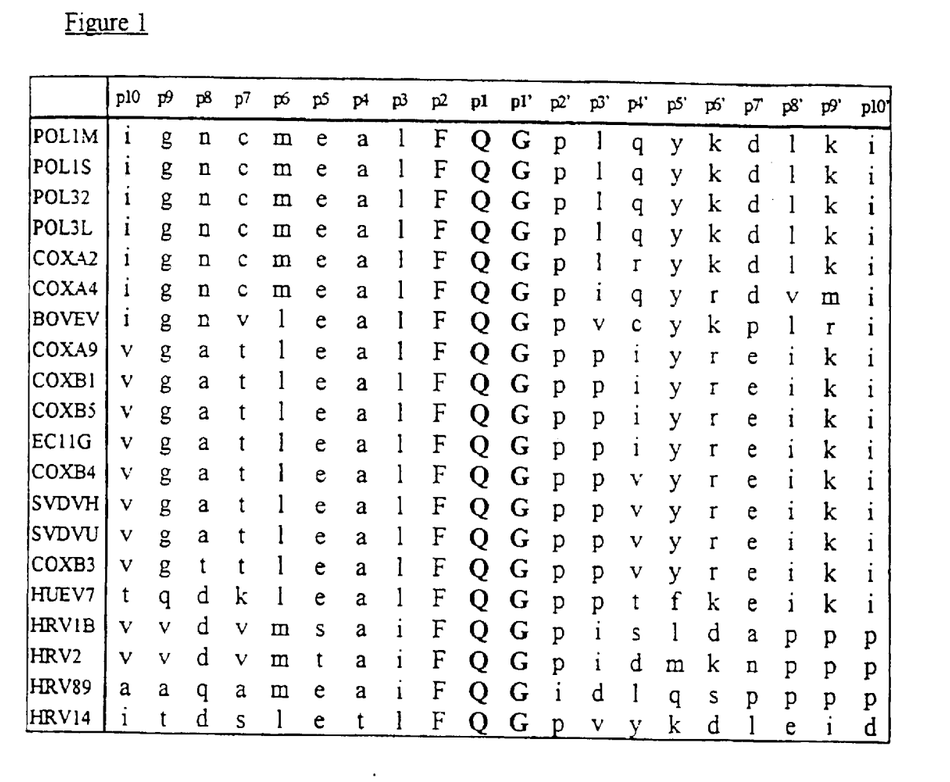
FIG. 1 shows amino acid sequences of oligopeptides capable of being formed into $R_1$ in accordance with an embodiment of the invention. Left column—the name of the virus as depicted by the GCG-code in the database. Right column—the appropriate amino acid sequences in one letter code.

Examples of $R_1$ sequences suitable in accordance with the second embodiment of the invention are specified in FIG. 1, wherein each sequence is depicted next to the name of the virus which 3C protease the respective $R_1$-carrying compound may inhibit.

$R_1$ can optionally be a fragment of at least 3 amino acids of the sequences specified in FIG. 1. Hereinafter, the term "amino acid" is understood to include the 20 naturally occurring amino acids; those amino acids often modified post-translationally in vivo, including for example hydroxyproline, phosphoserine and phosphothreonine; and other unusual amino acids including, but not limited to 2-aminoadipic acid, hydroxylysine, isodesmosine, norvaline, nor-leucine and ornithine. Furthermore, the term "amino acid" includes both D- and L-amino acids. The term "oligopeptide" refers to a series of amino acids linked by peptide bonds.

Other examples of suitable amino sequences of various picornaviruses may be construed according to the teachings of Cordingley et al *J. Biol. Chem.*, 265 (16): 9062–9065 (1990).

Suitable oligopeptides of 1 to 5 amino acids may be found by immobilizing an appropriate 3C picornavirus protease by attaching it to beads, for example, and then determining which peptides were able to specifically bind to the immobilized proteases. Such oligopeptides are suitable for serving as $R_1$ in the inhibitor of the second embodiment of the invention.

According to other embodiments, $R_1$ may be a pepidomimetic molecule, for example selected from one of the molecules stipulated in FIG. 2 prepared by peptidomimetic methods, which has similar binding properties to the active site as the oligopeptide of the second embodiment of the invention. Methods for preparing peptidomimetic compounds are well known in the art and are specified in Quantitative Drug Design, C. A. Ramsden Gd., Chapter 17.2, F. Choplin Pergamon Press (1992).

Specifically, pepidomimetic compounds can be prepared by altering the base structure of a portion of the ideal substrate for the HRV-14 (Human Rhinovirus 14) 3C protease, which has the amino acid sequence EALFQGPLQ (SEQ ID NO:1). This structure is altered by replacing at least the peptide bond between Q and G with various non-peptidic bonds, such as $CH_2$—NH, $CH_2$—S, $CH_2$—S=O, O=C.NH, $CH_2$—O, $CH_2$—$CH_2$, S=C—NH, CH=CH or CF=CH. The resulting moeity has a sufficiently similar structure to the preferred substrate for good binding to the active site of the protease, but is not readily cleavable by the enzyme, thereby remaining bound and inhibiting its activity. Hereinafter, the term "peptidomimetic" refers to an molecule which is not an oligopeptide, yet has a binding affinity to the protease active site which is at least as good as the native oligopeptide.

Alternatively and preferably, Z' and $R_1$ collectively form a ring system selected from the group consisting of $C_5$–$C_{10}$ heterocyclic ring system which may be saturated or unsaturated and which includes at least one nitrogen, oxygen or sulfur atom, and which may be additionally substituted with at least one, and more preferably 1–3, $R^{11}$ as defined above.

The compounds of the present invention have the advantage of strong selective protease inhibitory activity without substantial toxicity. Furthermore, the compounds of the present invention also display strong anti-viral activity. However, the mechanism of action of these compounds could also involve inhibition of other viral processes and stages of the virus life cycle. Hereinafter, the term "anti-viral" includes any effect which substantially interrupts, prevents or reduces any viral activity and/or stage of the virus life cycle, or which reduces or prevents infection by the virus in a subject, such as a human or lower animal, without regard to a particular mechanism of action such as inhibition of 3C protease activity.

Nowhere in the prior art is it taught or suggested that the compounds of the present invention have significant anti-viral activity, or that these compounds are 2A or 3C protease inhibitors. Indeed, the compounds of the present invention can be readily distinguished from those of the prior art both by their basic structure and by their efficacy. For example, as noted above, these compounds display greater anti-viral activity than DIF1. In U.S. Pat. No. 5,514,778, $IC_{50}$ anti-viral inhibitory activity requires mM quantities. By contrast, many of the compounds of the present invention have anti-viral activity with an $IC_{50}$ of only μM quantities, 3 orders of magnitude more potent. Not surprisingly, the structures of the two groups of compounds are also completely different.

Thus, the compounds of the present invention show clear advantages over prior art compounds.

BRIEF DESCRIPTION OF THE DRAWINGS

FIGS. 2A, 2B and 2C give examples of peptidomimetic moeities for $R_1$; and

DESCRIPTION OF PREFERRED EMBODIMENTS

The present invention relates to compounds which have strong anti-viral activity against picornavirus species. Furthermore, pharmaceutical compositions and methods of treatment of diseases caused by picornavirus species are also disclosed.

Synthesis of Compounds of the Present Invention

The compounds of the present invention can be synthesized according to procedures which are well known in the art.

A general example of a method of synthesis of the compounds of the present invention is as follows. Compounds of formula (I), where X is C=O, Z is hydroxyl, $R_3$ is OH and Z', Y and Y' are hydrogen, can be prepared with any $R_1$ group by implementation of the Hoesch reaction between resorcinol and the appropriate commercially-available nitrile, $R_1$—CN (Ruske, Freidel-Crafts and Related Reactions, ed by G. A. Olah, 1965, pp. 383–497). Likewise the Hoesch reaction performed with fluoroglucinol with the appropriate nitrile yields compounds of formula (I) where X is C=O, Z, Z' and $R_3$ are hydroxyl, and Y and Y' are hydrogen. Similarly, the same reactions performed with the appropriate nitrile and meta (lower) alkoxy-phenols, such as 3-hydroxyanisole or 5-methoxyresorcinol, also yields compounds of formula (I) where X is C=O, Z is hydroxyl, Z' is lower alkoxy, R3 is hydrogen or hydroxyl and Y and Y' are hydrogen.

Compounds of formula (I), where X is C=O, Z is hydroxyl and one or both of Y and Y' are Cl can be readily prepared by chlorinization of corresponding compounds, where either or both of Y and Y' are hydrogen, by using the reagent sulfuryl chloride (Masilamani and Rogic, *J. Org. Chem.* 46:4486–4489, 1981).

The following specific examples of particular methods of synthesis are intended for illustrative purposes only and are not meant to be limiting.

Compound 109

Formula IV, Z'=OH, Y=Y'=Cl, $R_3$=H

A solution of 2,6-dihydroxyacetophenone (152 mg, 1 mmole) in absolute methanol (1 ml), was diluted in anhydrous dichloromethane (10 ml). To the resultant clear solution was added dropwise a 1M solution of sulfuryl chloride in anhydrous dichloromethane (2 ml) at room temperature. After stirring at room temperature for 1.5 hours, the solvents were evaporated and the residue was purified by silica gel column chromatography with hexane:dichloromethane (30:70), to provide 80 mg of a brown-orange solid, M.P. 147.5° C. $^1$H NMR (DMSO-$^6$d, 200 MHz): δ 7.67 (s, 1H), 2.63 (s, 3H), MS (EI$^+$): 205.0 ($M^+$-$CH_3$, 100%), 220.0 ($M^+$, 47%).

Compound 21

Formula V, a 4:1 Mixture of Compounds 108 and 107, Respectively

Dihydroxyanisole (1.113 g, 7.9 mmole), hexanonitrile (1.60 ml, 13.2 mmol) and zinc chloride (700 mg) were dissolved in 50 ml of sodium-dried ether. The stirred solution was saturated with a steady stream of dry hydrogen chloride gas and after 5 minutes turned milky. 10 minutes later, a viscous orange oil separated, and the mixture was left overnight. The colorless solution was decanted and the oil was taken in 50 ml of ice-cold water. The resultant clear orange-red solution was extracted with ether (2×50 ml) and the aqueous phase was boiled on a hot-plate and concentrated to half the original volume ca. (30 ml). At this point, the solution became turbid, and upon cooling a brown-orange solid separated (810 mg), M.P. (air-dried) 100° C. Two products were apparent by TLC [(chloroform:ether 1:1). $R_f$=0.68 (major), $R_f$=0.76 (minor):(dichloroform). $R_f$=0.10 (major), $R_f$=0.33 (minor)]. $^1$H NMR (CD$_3$OD, 200 MHz): δ 5.95 (d, 2H: major), 5.90 (s, 2H; minor), 5.87 (d, 1H: major), 3.85 (s, 3H: major), 3.76 (s, 3H: minor), 2.99 (t, 2H: minor), 2.94 (t, 2H: major), 1.63 (m, 2H), 1.34 (m, 4H), 0.92 (3H, t). The product ratio was 4.3:1, as determined by NMR integration at δ 3.85 (major) vs δ 3.76 (minor), MS (EI$^+$): 238.1 ($M^+$, 18%), 167.0 ($M^+$-$C_5H_{11}$, 100%).

Compounds 107 and 108

Formula V

Z'=OH, $R_3$=OCH$_3$, Y=Y'=H (107)

Z'=OCH$_3$, $R_3$=OH, Y=Y'=H (108)

750 mg (3.15 mmol) of the isomeric methoxy-hexanoresorcinones mixture (compound 21) was loaded on a silica gel column equilibrated with dichloromethane. Fractions 6–7 (eluted with dichloromethane) contained pure (TLC) of the minor isomer. Evaporation of the solvent yield 78 mg of white solid, corresponding to compound 107. M.P. 121° C. TLC (dichloromethane), $R_f$=0.33. $^1$H NMR (CD$_3$OC, 200 MHz): δ 5.90 (s, 2H), 3.76 (s, 3H), 3.03 (t, 2H), 1.65 (t, 2H), 1.35 (m, 4H), 0.91 (t, 3H). MS (EI$^+$): 167.1 (M$^+$-C$_5$H$_{11}$, 100%), 238.2 (M$^+$, 15%). Fractions 10–12 (eluted with 4:1 ethyl acetate:dichloromethane) contained pure (TLC) major isomer. Removal of the solvents yielded 384 mg of grayish solid, corresponding to compound 108, M.P. 109° C. TLC (dichloromethane), $R_f$=0.10. $^1$H NMR (CD$_3$OD, 200 MHz): δ 5.94 (d, 1H), 5.87 (d,1H), 3.84 (s, 3H), 2.93 (t, 2H), 1.62 (t, 2H), 1.34 (m, 4H), 0.92 (m, 3H). MS (EI$^+$): 238.2 (M$^+$, 39%). 167.1 (M$^+$-C$_5$H$_{11}$, 100%).

Compound 15

Formula V, Z'=OH, R$_3$=OCH$_3$, Y=Y'=Cl

A stirred solution of 2,6-dihydroxy-4-methoxyhexanophenone (cf. compound 107: 28 mg, 0.12 mmol) in absolute methanol (0.25 ml), was diluted in anhydrous dichloromethane (10 ml) at room temperature. A 1M solution of sulfuryl chloride in anhydrous dichloromethane was added dropwise (0.26 ml, 2.2 mmol), and the color of the resultant mixture was observed to change from faint yellow to bright vivid yellow within seconds. 20 minutes later, the solvents were evaporated and residual sulfuryl chloride was removed in vacuo, resulting in yellow crystals (38 mg). M.P. 101° C. $^1$H NMR (CDCl$_3$): δ 10.32 (s, 2H), 3.98 (s, 3H), 3.13 (t, 2H), 1.71 (t, 2H), 1.35 (m, 4H), 0.91 (t, 3H) [identical to spectrum described by Masento et al., 1988, Biochem. J. 256: 23–28], MS (EI$^+$): 306.0 (M$^+$, 21%), 235.0 (M$^+$-C$_5$H$_{11}$, 100%).

Compound 16

Formula V, Z'=OCH$_3$, R$_3$=OH, Y=Y'=Cl 2,4-dihydroxy-6-methoxyhexanophenone (cf. compound 108: 10 mg, 0.04 mmol) was reacted with sulfuryl chloride in a manner analogous to that described in compound 15 above. The product was vacuum-dried, resulting in orange crystals (12 mg). $^1$H NMR (CDCl$_3$): δ 14.02 (s, 1H), 6.51 (s, 2H), (s, 1H), 3.91 (s, 3H), 3.05 (t, 2H), 1.69 (t, 2H), 1.32 (m, 4H), 0.89 (t, 3H).

Compound 22

Formula V, Z'=OH, R$_3$=OH, Y=Y'=H

The Hoesch reaction was employed following the general procedure of Howells and Little (Howells, H. P. and Little, J. G., 1932, J. Am. Chem. Sco. 54: 2451–2453), with the addition of an initial reaction of hexanitrile in the absence of aromatic reactant, a means of improving the yield (see March, Advanced Organic Chemistry, 1968, p. 424). Through a stirred solution of hexanonitrile (1.37 ml, 11.0 mmol) and zinc chloride (600 mg) in 30 ml of dry ether containing 1M hydrogen chloride, was passed a stream of dry hydrogen chloride gas at room temperature. After 0.5 hour, the following were added: phloroglucinol (1.0 g, 7.9 mmole), sodium-dried ether (18 ml) and zinc chloride (400 mg), and the mixture was saturated with dry gaseous hydrogen chloride. During the next 0.5 hour, the solution turned milky, and red oily droplets appeared. In the course of another 0.5 hour, the mixture cleared. The resultant red-wine solution was left overnight, and subsequently diluted by the addition of ice-cold water (40 ml). The aqueous phase was extracted with ether (3×30 ml), and boiled on a hot-plate. After a few minutes, a gray sediment appeared. The solution was further boiled, the initial volume being reduced by half. Upon cooling, 1.13 g of a brown solid was obtained. $^1$H NMR (CD$_3$OD, 200 MHz): δ 5.80 (s, 2H), 3.02 (t, 2H), 1.65 (m, 2H), 1.34 (m, 4H), 0.92 (3H, t).

Compound 23

Formula IV, Z'=OCH$_3$, R$_3$=OH, Y=Y'=H

Dihydroxyanisole (0.500 g, 3.57 mmol), zinc chloride (170 mg) and acetonitrile (0.214 ml, 4.10 mmol) in 35 ml of dry ether were stirred at room temperature. A steady stream of dry gaseous hydrogen chloride was passed through the mixture, and after 10 minutes the solution turned cloudy and a brown oil separated. In the course of another 5 minutes, the solution above the oil cleared. After 2.5 hours, 25 ml of cold water were added, and the mixture was left overnight. The aqueous phase was extracted with water and concentrated by boiling on a hot-plate. Pink crystals began to form after the volume of the aqueous phase was reduced by half, and accumulated on cooling, resulting in 94 mg, 68 mg of which were recrystallized in water to yield 34 mg of pink cyrstals. M.P. 201–202° C. TLC (dichloromethane:ether 7:3). $R_f$=0.57. UV, λ=287.3 nm (εmM=18.5 cm$^{-1}$ M$^{-1}$). $^1$H NMR (CDCl$_3$, 200 MHz): δ 12.0 (s, 1H; chelated) [DMSO-d$_6$: δ 13.82 (s, 1H; chelated)], 7.38 (s, 1H, broad) [DMSO-d$_6$; δ 9.2–11.8 (s, 1H; broad)], 5.96 (s, 1H), 5.65 (s, 1H), 3.87 (s, 3H), 2.61 (s, 3H).

Compound 25

Formula IV, Z'=OCH$_3$, R$_3$=OH, Y=Cl, Y'=H

To a solution of 2,4-dihydroxy-6-methoxy acetophenone (cf. compound 23: 30 mg, 0.16 mmol) in ether (7 ml) was added sulfuryl chloride (13 μL, 0.20 mmol)) in ether (70 μL) dropwise, over 5 minutes, 2 hours later, a further portion of sulfuryl chloride (13 μL, 0.20 mmol) was added directly and after another hour a sediment appeared, and the mixture was left overnight at −20° C. After evaporation of the ether, a white powered remained, which after recrystallization (ethyl acetate) gave 12 mg of yellow odorless crystals (0.500 g, 3.57 mmol). M.P. 187.5–189° C. $^1$H NMR (DMSO-d$_6$): δ 14.6 (s, 1H; chelated), 11.4 (s, 1H), 6.19 (s, 1H), 3.83 (s, 3H), 2.56 (s, 3H [integration confirmed in CD$_3$OD]), MS (EI$^+$): 216.0 (M$^+$, 49%), 167.1 (M$^+$-CH$_3$, 100%).

Compound 112

Formula V, Z'=OH, R$_3$=OH, Y=Cl, Y'=H

To a stirred solution of 2,4,6-trihydroxy-hexanophenone (compound 22 (60 mg, 0.25 mmol) in absolute methanol (0.5 ml) at room temperature, was added anhydrous dichloromethane (10 ml) and a 1M solution of sulfuryl chloride in dichloromethane (0.50 mmol). After 10 minutes, the solvents were evaporated and 17 mg of the residue were purified by column chromatography (dichloromethane) to provide 5 mg. $^1$H NMR (CD$_3$OD): δ 5.49 (s, 1H), 3.11 (t, 2H), 1.68 (t, 2H), 1.37 (m, 4H), 0.93 (t, 3H).

Compound 111

Formula IV, Z'=OH, R$_3$=OH, Y=Y'=Cl

A stirred solution of 2,4,6-trihydroxy-acetophenone (339 mg, 2.0 mmol) in absolute methanol (05 ml), was diluted in anhydrous dichloromethane (10 ml) at room temperature (19° C.). A 1M solution of sulfuryl chloride in anhydrous dichloromethane was added dropwise (2 mmol), and the solution was observed to become turbid with a small amount of solid. After 1 hour, another portion of sulfuryl chloride 1M solution in dichloromethane was added (2 mmol), and after 4 more hours, the solvents were evaporated, resulting in a yellowish solid, 600 mg of which was purified by flash chromatography (dichloromethane to 2:1 dichloromethane: ethyl acetate) to yield 86 mg crystalline yellow-orange solid. $^1$H NMR (CDCl$_3$): δ 9.30 (s, 1H), 2.70 (s, 3H).

Compound 105

Formula VIII, Z'=R$_3$=OH, Y=Cl, Y'=H,

To a stirred solution of phloretin (40 mg, 0.146 mmol) in absolute methanol (10 ml), at room temperature, was added 292 μL of a 1M solution of sulfuryl chloride in anhydrous dichloromethane (0.292 mmol), and the yellow solution was observed to become brighter. After 1 hour, the methanol was evaporated and the resultant brownish solid (152 mg) was purified by column chromatography (4:1 chloroform:ethyl acetate), to yield 15 mg of brown-purple sheaths. $^1$H NMR (CD$_3$OD): δ 7.06 (d, 2H), 6.69 (d, 2H), 5.49 (s, 1H), 3.34 (t, 2H), 2.88 (t, 2H).

Compound 100

Formula XII, R$_3$=OH, Y=Y'=Cl

A solution of sulfuryl chloride (0.35 ml, 2.15 mmol) in dichloromethane (5 ml) was added to 250 mg Chrysin (5,7-dihydroxyflavone: 0.984 mmol), and the resultant slurry was stirred vigorously at room temperature. After 30 minutes, 0.20 ml of a solution of pyridine (1.24 mmole) in chloroform was added dropwise and the mixture was allowed to stir for a further 3 hours. After removal of solvents, diethyl ether was added, resulting in the sedimentation of a flaky yellow solid (210 mg). M.P. 301° C. $^1$H NMR (CMSO-$^6$d, 200 MHz): δ 8.21 (dd, 2H), 7.60 (m, 3H), 7.20 (s, 1H). MS (EI$^+$): 322.1 (M$^+$, 100%).

Activity of Compounds of the Present Invention

The following examples of the activity of the compounds of the present invention are meant to be illustrative and are not intended to be limiting in any way.

EXAMPLE 1

Inhibition of 3C Activity by DIF1

The ability of DIF1 to inhibit the cleavage activity of the 3C protease was measured. DIF1 storage inhibited the ability of 3C protease to cleave the test substrate. The experimental method was as follows.

First, the synthesis of DIF1 was carried out according to the procedure of Masento et al., *Biochem. J.,* 25b, 23–28 (1988).

Next, the inhibition of 3C protease activity was measured by using a cleavage assay. A synthetic N-acetylated 10-mer peptide possessing the consensus sequence for cleavage by Rhinovirus protease 3C (Queens's University, Ontario) was used as a substrate. Specific cleavage of this peptide [(N-Ac)Arg-Ala-Glu-Leu-Gln-Gly-Pro-Thr-Asp-Glu] (SEQ ID NO:2) by HRV 3C provided two pentapeptides. In a typical experiment 80 μg of peptide, dissolved in 100 mM TRIS (pH 8) and 100 mM NaCl, was incubated at 35° C. with 2.5 μg of HRV 3C protease with and without DIF1, to give a total volume of 30 μl. In both cases 3C was suspended in a buffered solution (40 mM Tris-HCL, pH 8.0, 100 mM, NaCl, 1 mM DTT, 1 mM EDTA), 2.5 mg of DIF1 (dissolved in 1 ml of ethanol) was used, corresponding to a concentration of 270 μM. Inhibitory effects due to the organic solvent were not observed; nevertheless, 10 μl of ethanol were added to the control. Aliquots were drawn at short intervals (within ca. 40 min.) and quenched with an equal volume of 1% TFA in Methanol (HPLC grade).

The digestion mixtures obtained from the cleavage assay were separated by reverse phase HPLC (Pharma Biotech Resource™ R.P.C. 15 μm beads 30×6.4 mm) using a 20–80% gradient of 0.1% TFA in MeOH (Carlo-Erba) in 5 minutes (flow rate of 1 ml/min). Simultaneous detection at 280 and 215 nm provided additional resolution (Pharmacia LKB RSD, Uppsala, Sweden), as only one of the pentapeptide cleavage products retains absorption at 280 nm, the tyrosine-containing fragment GPYDE (SEQ ID NO:3).

The degree of 3C protease inhibition by DIF1 was found by integration of peak areas under the 280 nm absorption curve. The degree of cleavage was calculated as the ratio of peak areas corresponding to peptide alone and peptide plus GPYDE (SEQ ID NO:3) product. Quantification was based on the initial, linear portion of the absorption curve, which represents less than 20% cleavage.

In the absence of DIF1, there was a marked increase in the level of peptide digestion products, compared to corresponding results obtained in the presence of DIF1. Thus, DIF1 clearly has an inhibitory effect on the cleavage activity of the 3C protease.

Furthermore, the rate of substrate cleavage decreased significantly in the presence of 270 μM DIF1. Ki was calculated to be 220 μM. Thus, clearly DIF1 strongly inhibited the activity of the 3C protease, with an efficacy in the μM range.

An additional assay was performed as follows in order to confirm the above results.

HRV 3C Protease Inhibition Assay—HPLC Method

Materials:

Protease: Recombination HRV-1A 3C protease was produced in *E. Coli* [BL21(DE3)pLysS] containing the protease gene under the control of an inducible T7 expression vector (Studier, F. W. et al., 1990, in *Methods of Enzymology* (Goeddel, D. V., ed.). Use of T7 RNA polymerase to direct expression of cloned genes, 185: 60–89). The protease was obtained in soluble form (following cell lysis) by reducing the temperature post-induction (0.4 mM IPTG) from 37° C. to 25° C. as described by Harris et al. (Harris, K. S. et al., 1992, Purification and characterization of poliovirus polypeptide 3CD, a proteinaceous and a precursor for RNA polymerase. *F. Virol.* 66: 7481–7489). The lysate in 20 mM Tris, pH 8.0, 30 mM NaCl, 1 mM EDTA and 1 mM DTT was kept at −20° C. and diluted to a final concentration of 3.3 μM.

Substrate: Peptide of sequence [N-Ac)Arg-Ala-Glu-Leu-Gln-Gly-Pro-Tyr-Asp-Glu-NH$_2$] (SEQ ID NO:2), representing the consensus sequence for cleavage by HRV-3C., was obtained from Peptide Core Facility (Queens's University, Ontario). Stock solutions of 10 mg/ml were prepared in 100 mM Tris-HCl (pH 8.0).

Compounds assayed for inhibition were dissolved in 95% EtOH in an amount sufficient to make 8–100 mM stock solutions.

Reactions:

Assayed compound (5.5 μL) and recombinant HRV-3C protease were mixed in buffer containing 50 mM Tris, pH 8.0 and 3 mM dithiothreitol (final EtOH concentration of 5%). A control mixture was prepared in a similar manner, containing 95% EtOH in place of compound. Reactions were initiated, followed overnight incubation (30±2° C.), by the addition of peptide substrate (final concentration of 810 $\mu$M). Aliquots were withdrawn at timed intervals (typically, 4, 8 and 12 minutes post-initiation) and quenched by mixing with ice-cold trichloroacetic acid (final concentration of 10%). Quenched aliquots were left on ice for further 30 minutes and centrifuged (14,000 ppm, 5'). The supernatant was further diluted by the addition of 7 volumes of HPLC solvent A (0.1% TFA), prior to loading (80 $\mu$L) via autosampler onto HPLC (Waters 626 LC system). Intact peptide [Retention time ($R_t$) 17'] was separated from C-terminal fragment [NH2-Gly-Pro-Tyr-Asp-Glu(NH2) (SEQ ID NO:3), confirmed by Fab+ mass spectrometry: $R_t$ 8'], on a C18 column (Vydac, 4.6·250 mm, 5 $\mu$m particles). The following discontinuous gradient of A to B (20% $CH_1CN$, 0.1% TFA) was employed at constant flow (1.5 ml/min): i) 0–35% B in 2' at a hyperbolic gradient of steepness 3 (1–11 scale, 6 being linear) ii) A linear gradient of 35–50% B from 2-8', iii) A linear gradient of 50–87.5% B from 8-9' and iv) Isocratic 87.5% B from 9-17'. Tyrosine fluorescence (275 excitation, 310 emission: Bagshaw, 1987) was measured continuously by a Water 474 fluorescence detector. Integration of peak areas corresponding to control and inhibitor-containing cleavage mixtures (Millenium Chromatography Manager 2020 software, version 2.10, Waters, Millipore Corp.) provided percent activity values at several time-points. Extrapolation of these values by linear regression provided $IC_{50}$ values directly. Ki values corresponding to inhibitor-enzyme dissociation constants were determined using a Km value of 1.9 mM (Determined by HPLC method). The HRV-1A 3C protease inhibitory activity of representative compounds of the invention is shown in the table below.

| # | Formula | Z | Y | $Y^1$ | $R_3$ | Ki ($\mu$M) |
|---|---|---|---|---|---|---|
| 1 | X (Dioxybenzone) | H | H | H | OMe | 4700 ± 900 |
| 3 | (Juglone) | | | | | 630 ± 70 |
| 15 | II(DIF-1) | OH | Cl | Cl | OMe | 460 ± 80 |
| 16 | V (iso-DIF-1) | OMe | Cl | Cl | OH | 390 ± 30 |
| 17 | IX | OH | Cl | Cl | OMe | 1670 ± 710 |
| 18 | VI | OH | Cl | Cl | OMe | 860 ± 230 |
| 19 | VII | OH | Cl | Cl | OMe | 690 ± 160 |
| 20 | V | OH | Cl | Cl | OH | 460 ± 60 |
| 21 | V | OMe/OH | H | H | OH/OMe | >15,000 |
| 25 | IV | OMe | Cl | H | OH | 3000 ± 1500 |

EXAMPLE 2

Specificity of Inhibition by DIF1

The specificity of DIF1 as an enzyme inhibitor was tested using cleavage assays for a number of other enzymes, including elastase, cathepsin B, chymotripsin, papain and ficin A. Elastase was particularly important because it is present in red blood cells, so that inhibition of its activity could potentially be highly toxic. The results showed that DIF1 does not non specific inhibition of other the activity of other enzymes. The experimental method was as follows.

The cleavage activity of elastase was determined in 0.1 M Tris-HCl pH 7.0 buffer containing 20 $\mu$g/ml enzyme and its synthetic substrate. N-succinyl-Ala-Ala-Ala-p-nitroanilide. 50 mM DIF1 did not inhibit the cleavage activity of elastase.

The cleavage activity for cathepsin B was assayed according to the method of Bajowski an Frankfater (*Anal. Biochem.* 68:119 (1975)). Chymotripsin was assayed in 0.1M KPi buffer pH 7.0 containing 0.04 $\mu$g/ml enzyme and 200 $\mu$M N-benzyl-L-tryosine ethyl ester (from a 20 mM stock in dimethyl sulfoxide). The reaction was monitored by spectrophotometry at 256 nm.

Papain and Ficin were incubated for one hour in an activation solution containing 0.1 M KPi buffer pH 7.0. 0.5 mM cysteine, 20 mM EDTA and 65 $\mu$g enzyme. The assays were carried out by adding 20 $\mu$l aliquots from the activation mix to 0.1 M KPi buffer pH 7.0, containing 12.5 nM N-CBZ-p-Nitrophenyl ester. The reaction was monitored by spectrphotometry at 405 nm. The results showed that all DIF1 concentrations tested were found not to effect the protealytic activity of cathepsin B, chymotripsin, papain and ficin A.

Thus, clearly DIF1 does not show non-specific or undesirable inhibitory activity for other enzymes such as elastase.

EXAMPLE 3

Derivatives of DIF1 and Inhibition of 3C Protease Activity

The inhibitory activity of a number of derivatives of DIF1 of formula III and IV was determined as described above for DIF1. Ki for the compounds of formula III and IV was found to be 150 $\mu$M and 154 $\mu$M respectively, compared to 220 $\mu$M for DIF1. Thus, the derivatives of DIF1 may feature a better enzyme inhibitory activity than the native compounds.

EXAMPLE 4

Inhibition of Virus in Whole-Cell Assay

The ability of DIF1 derivatives to inhibit viral activity was measured in whole cells, to examine the ability of the compounds to inhibit the viral life cycle. Interestingly, many of the compounds displayed greater anti-viral activity than inhibition of protease activity, indicating that the compounds may be acting as a site other than the 3C protease. The experiment method was as follows.

H1-HeLa cells, obtained from ATCC (F-13824, 1958-CRL) were cultured in MEM (Minimum Essential Medium) supplemented with 10% heat-inactivated fetal calf serum (FCS) by incubation at 37° C, 5% $CO_2$ (Biological Industry, Kibbuts Beit HaEmek, Israel).

96 well plates were seeded to 90% confluency. After 12–24 hrs of incubation, the cell's monolayer was washed with phosphate-buffered saline (PBS), and the cells were subsequently infected with ten-fold dilutions in PBS (log10) of human rhinovirus 14, strain 1059, obtained from ATCC.

For each concentration of compound, three rows of wells containing various dilutions of virus were used. After 1 h of incubation at room temperature, medium containing 3% FCS and various concentrations of compound to be tested was placed in the well. After 2 days incubation at 34° C, 5% $CO_2$, the cells were fixed by 10% formaldehyde and stained with methylene blue to determine cell viability. The cytopathic effect of non-viable cells was arbitrarily set to 100% for the untreated viral infection, so that the effect of each compound on cell viability was determined according to this baseline. Each experiment was performed 5 times for each compound, and the inhibition of cytopathic effect ($ICE_{50}$) for inhibition of viral activity was calculated. Compounds were tested at concentrations lower than 50% toxic dose ($TD_{50}$) previously found. $ICE_{50}$ refers to the concentration in which 50% of the cells remain viable after viral infection.

A number of compounds of formula IV were assayed for their anti-viral activity, with the results given in Table 1.

Certain substituents were shown to substantially increase the anti-viral activity of the compound, as indicated below.

TABLE 1

Compounds of Formula IV

| Z' | Y' | $R_3$ | Y | $ICE_{50}$ ($\mu$M) | $TD_{50}$ ($\mu$M) |
|---|---|---|---|---|---|
| H | H | H | H | | 30 |
| H | H | OH | H | | 40 |
| H | OH | H | H | | 5 |
| OH | H | H | H | | 5 |
| OH | Cl | H | Cl | 1250 | 5000 |
| OH | Cl | OH | Cl | | 1000 |
| O-CH₃ | H | OH | H | | 220 |
| O-CH₃ | H | OH | Cl | 11 | 22 |

A number of compounds of formula V were also assayed. The results are given below, in Table 2.

TABLE 2

Results for Formula V

| Z' | Y' | $R_3$ | Y | $IC_{50}$ | $TD_{50}$ |
|---|---|---|---|---|---|
| OH | H | OH | H | 155 | 625 |
| OH | Cl | O-CH₃ | Cl | 7.5 (3) | 30 |
| OH | Cl | OH | Cl | | 1875 |
| OH | H | O-CH₃ | H | | 125 |
| O-CH₃ | H | OH | H | 12 (2) | 250 |
| O-CH₃ | Cl | OH | Cl | 3 (2) | 40 |
| H | H | OH | H | 20 | 170 |
| OH/O-CH₃ (4:1 ratio) | H | OH/O-CH₃ (4:1 ratio) | H | 10 | 50 |

Other examples of compounds of other formulas were tested and the results were as follows.

| Formula | Z' | Y' | $R_3$ | Y | $ICE_{50}$ | $TD_{50}$ |
|---|---|---|---|---|---|---|
| VI | OH | Cl | O-CH₃ | Cl | 20 | 80 |
| VII | OH | Cl | OH | H | | 200 |
| VII | OH | Cl | O-CH₃ | Cl | | 40 |
| IX | OH | Cl | O-CH₃ | Cl | | 80 |
| XII | — | H | H | H | | 1000 |
| XII | — | Cl | H | Cl | 2.5 | 100 |
| VIII | OH | H | OH | Cl | 40 | 150 |
| VIII | OH | H | OH | H | | 160 |
| XIV | H | NO₂ | H | NO₂ | | 1875 |

Thus, clearly many of these compounds of the different formulas have significant anti-viral activity.

EXAMPLE 5

Compositions of the Present Invention

The compounds of the present invention can be administered to a subject in a number of ways, which are well known in the art. Hereinafter, the term "subject" refers to the human or lower animal to whom the compound was administered. For example, administration may be done topically (including ophtalmically, vaginally, rectally, intranasally), orally, or parenterally, for example by intravenous drip or intraperitoneal, subcutaneous, or intramuscular injection.

Formulations for topical administration may include but are not limited to lotions, ointments, gels, creams, suppositories, drops, liquids, sprays and powders. Conventional pharmaceutical carriers, aqueous powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions which may also contain buffers, diluents and other suitable additives.

Pharmaceutically acceptable carriers are well known in the art and are disclosed, for instance, in *Sprowl's American Pharmacy,* Dittert, L. (ed.). J. B. Lippincott Co., Philadelphia, 1974, and *Remington's Pharmaceutical Sciences,* Gennaro, A. (ed.), Mack Publishing Co., Easton, Pa., 1985.

Pharmaceutical compositions of the compounds of the present invention, or of pharmaceutically acceptable salts thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution, but a lipophilic carrier, such as propylene glycol optionally with an alcohol, may be more appropriate for compounds of this invention. Examples of suitable diluents are normal isotonic saline solution, standard 5% dextrose in water of buffered sodium or ammonium acetate solution. Such a formulation is especially suitable for parenteral administration, but may also be used for oral administration or contained in a metered dose inhaler or nebulizer for insufflation. It may be desirable to add excipients such as ethanol, polyvinylpyrrolidone, gelatin, hydroxy cellulose, acacia, polyethylene glycol, mannitol, sodium chloride or sodium citrate.

Alternatively, the compounds of the invention may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, soy bean oil, peanut oil, olive oil, glycerin, saline, ethanol, and water. Solubilizing agents, such as dimethylsulfoxide, ethanol or formamide, may also be added. Carriers, such as oils, optionally with solubilizing excipients, are especially suitable. Oils include any natural or synthetic non-ionic water-immiscible liquid, or low melting solid, which is capable of dissolving lipophilic compounds. Natural oils, such as triglycerides are representative. In fact, another aspect of this invention is a pharmaceutical composition comprising a compound of formula (I) and an oil.

Solid carriers include starch, lactose, calcium sulfate dihydrate, terra alba, magnesium stearate or stearic acid, talc, pectin, acacia, agar or gelatin. Solubilizing agents, such as dimethylsulfoxide or formamide, may also be added. The carrier may also include a sustained release material such as glyceryl monostearate or glyceryl distearate, alone or with a wax. The pharmaceutical preparations are made following the conventional techniques of pharmacy involving milling, mixing, granulating, and compressing, when necessary, for tablet forms: or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, a pulverized powder of the compounds of this invention may be combined with excipients such as cocoa butter, glycerin, gelatin or polyethylene glycols and molded into a suppository. The pulverized posers may also be compounded with an oily preparation, gel, cream or emulsion, buffered or unbuffered, and administered through a transdermal patch.

Nasal administration of the compounds of the invention may also be desired especially for the treatment of common cold and allergic rhinivity.

Dosing is dependent on the severity of the symptoms and on the responsiveness of the subject to the compound of the present invention. Persons of ordinary skill in the art can easily determine optimum dosages, dosing methodologies and repetition rates.

EXAMPLE 6

Methods of Treatment with Compounds of the Present Invention

Compounds of the present invention, when prepared according to the formulations described in Example 5, are suitable for the treatment of a number of different diseases. These diseases include those caused by the following viruses: the rhinoviruses (the common cold), enteroviruses such as poliovirus, coxsackievirus and echovirus, hepatitis A, cardioviruses such as encephalomyocarditis virus and meningovirus, and apthoviruses such as the virus for the foot-and-mouth disease.

The compositions used for treatment of these diseases preferably include a pharmaceutical carrier as described in Example 5. Preferably, the compositions are administered until a defined endpoint is reached, such as the absence of a particular virus, reduction or absence of symptoms of a disease caused by the virus, or prevention of infection of the subject by the virus.

EXAMPLE 7

Method of Manufacture of a Medicament Containing an Anti-Viral Compound

The following is an example of a method of manufacturing a medicament for treating a disease caused by a picornavirus. First, a compound of formula I is synthesized in accordance with good pharmaceutical manufacturing practice. Next, the compound of formula I is placed in a suitable pharmaceutical carrier, as described in Example 5 above, again in accordance with good pharmaceutical manufacturing practice.

EXAMPLE 8

Detection of a Picornavirus

The present invention also concerns a method for the detection of picornaviral infection. According to the method of the invention a compound of the invention bearing a detectable label (for example attached to $R_3$), is incubated with a sample, suspected of containing picornaviruses, under conditions enabling binding of the compound to proteases. Preferably the sample should be treated with a lysing agent in order to release the picornavirus proteins from inclusion bodies. Then it is determined whether the labeled compounds of the invention are bound to any proteins in the assay. A positive answer (beyond a predetermined control level) is indicative of the presence of a picornavirus in the assayed sample.

Since the compounds of the invention may be tailored to bind specifically to a desired species of picornavirus, by modifying $R_1$, it is possible according to the detection method of the invention not only to determine the presence of a virus, member of the picornavirus family, in the sample but also to determine the specific species of the picornavirus to which it is bound.

It will be appreciated that the above descriptions are intended only to serve as examples, and that many other embodiments are possible within the spirit and the scope of the present invention.

---

SEQUENCE LISTING

```
<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: CONSENSUS
      CLEAVAGE SEQUENCE FOR RHINOVIRUS

<400> SEQUENCE: 1

Glu Ala Leu Phe Gln Gly Pro Leu Gln
  1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: CONSENSUS
```

```
                CLEAVAGE SEQUENCE FOR RHINOVIRUS

<400> SEQUENCE: 2

Arg Ala Glu Leu Gln Gly Pro Tyr Asp Gl